US005758420A

United States Patent [19]
Schmidt et al.

[11] Patent Number: 5,758,420
[45] Date of Patent: Jun. 2, 1998

[54] PROCESS OF MANUFACTURING AN ANEURYSM CLIP

[75] Inventors: Ferenc J. Schmidt, Bryn Mawr, Pa.; Kevin P. Maughan, Sanibel, Fla.

[73] Assignee: Florida Hospital Supplies, Inc., Fort Myers, Fla.

[21] Appl. No.: 632,483

[22] PCT Filed: Oct. 20, 1993

[86] PCT No.: PCT/US93/10054

§ 371 Date: Jun. 4, 1996

§ 102(e) Date: Jun. 4, 1996

[87] PCT Pub. No.: WO95/10983

PCT Pub. Date: Apr. 27, 1995

[51] Int. Cl.$^6$ .............. B21F 3/00; B21K 29/00; B21D 7/00
[52] U.S. Cl. .............. 29/896.9; 72/128; 72/130; 72/137; 72/275; 72/342.8; 72/364; 72/371; 72/700; 140/82; 148/670; 148/671; 606/157
[58] Field of Search .............. 29/896.9; 24/545, 24/552; 140/82, 89, 103; 72/128, 129, 130, 136, 137, 275, 278, 286, 342.8, 364, 371, 700, 702; 148/670, 671; 606/155, 156, 157, 158

[56] References Cited

U.S. PATENT DOCUMENTS

| | | |
|---|---|---|
| 3,394,036 | 7/1968 | Parris . |
| 3,511,719 | 5/1970 | Nation . |
| 4,765,335 | 8/1988 | Schmidt et al. . |
| 4,952,236 | 8/1990 | Wang et al. . |
| 4,966,603 | 10/1990 | Focelle et al. . |
| 4,989,439 | 2/1991 | Ewert et al. . |
| 5,053,045 | 10/1991 | Schmidt et al. . |
| 5,125,986 | 6/1992 | Kimura et al. . |
| 5,201,967 | 4/1993 | Schutz et al. . |

OTHER PUBLICATIONS

J.C. Chang, "Forming Ti–6A1–4V Sheet Metal in Four Heat Treated Conditions," 1970, pp. 1053–1063, The Science, Technology and Application of Titanium.(R. Jaffe & N. Promisel, eds.).

A. M. Sabroff et al., "The Cold Extrusion of Titanium," Feb. 1956, pp. 1 and 33, Wright Air Development Center.

R.J. McClivtick et al., "Physical Metallurgy and Heat Treatment of Titanium Alloys," 1956, pp. 43–54, Mallory–Sharon Titanium Corporation.

Primary Examiner—S. Thomas Hughes
Attorney, Agent, or Firm—Ratner and Prestia

[57] ABSTRACT

A process for manufacturing an aneurysm clip (10) having a coil spring (22), a first arm (26) ending in a first clamping jaw, and a second arm (34) ending in a second clamping jaw (40). The method includes: (a) providing a cylindrical starting rod (1) of titanium or titanium alloy; (b) cold drawing the rod to reduce its diameter and increase its strength; (c) cutting the rod to form a single resilient member (12); (d) winding the member about a mandrel to form the coil spring while incorporating the deflection of the arms into the clamping force of the clip; (e) shaping the member into two end sections (16) forming the clamping jaws and two connecting sections (18) forming connecting elements for the jaws; (f) coining the two end sections of the member a temperature between 900 and 1000 degrees F.; and (g) bending the clamping jaws into a position assuring that the clamping jaws are parallel when clamped onto tissue (70).

47 Claims, 6 Drawing Sheets

PROCESS OF MANUFACTURING AN ANEURYSM CLIP

FIELD OF THE INVENTION

This invention relates generally to a process of manufacturing aneurysm clips and, more particularly, to a process of manufacturing a titanium or titanium alloy aneurysm clip incorporating the steps of cold drawing, coining, and bending a single, continuous, solid, elongated, resilient, cylindrical member to form the clip.

BACKGROUND OF THE INVENTION

A cerebral aneurysm clip is a surgical instrument which clamps the base part of a cerebral aneurysm to temporarily or permanently isolate it from the cerebral artery. For this purpose, the clip must maintain the clamping pressure with high reliability as long as desired without injury to the wall of the blood vessel. Such injury might be caused, for example, by a shearing action of the clamping jaws, which results from improper jaw alignment; improper clamping pressure; foreign material trapped in cracks and crevices formed in the clip design; surface imperfections on the clip material which can tear tissue; or the use of unsuitable materials to manufacture the clip.

A number of different materials are used to manufacture cerebral aneurysm clips. Such materials include, for example, stainless steel and chrome-cobalt alloy steel. These materials interfere with important diagnostic techniques such as magnetic resonance imaging (MRI or NMR), MRA, and CT-Scanning due to image degradation (haloing, starbursts, and "Black-Hole" obscuring) caused by the magnetic characteristic and high density of the materials. Furthermore, the significant magnetic susceptibility of these materials presents the danger that such clips will move in the intense magnetic fields created.

Titanium and some titanium alloys (specifically, the Ti 6-4 alloy of about 6% aluminum, 4% vanadium, and the remainder titanium ) are most desirable for implants because they are inert, are compatible with body fluids, are non-magnetic, and do not degrade the image. Having such qualities, CP (Chemically Pure) Titanium (ASTM F64-89) and the Ti 6-4 alloy have been widely acknowledged in medical literature and have been approved by the Federal Drug Administration for implants in human beings. The great difficulty in forming CP Titanium and Ti 6-4 alloys, however, has prevented their wide-spread use in aneurysm clips.

To provide satisfactory and prolonged service when properly implanted, a cerebral aneurysm clip should satisfy most, and preferably all, of the following criteria:

1. The clamping pressure of the jaws of the clip should be sufficient to isolate the aneurysm but not so high as to damage the blood vessel wall during either temporary or permanent implantation;
2. The clamping pressure of the clip should remain constant over time to prevent displacement or slipping of the clip;
3. The clip should be as small as possible to facilitate permanent implantation in the brain;
4. The material of construction of the clip should be nonmagnetic and have low density to prevent interference with MRI and CT-scan imaging;
5. The shape of the clip should not obstruct the surgeon's view during implantation;
6. To prevent unintentional tears and pressure points, the surface of the clip should be smooth and jagged edges should be absent;
7. The surface of the clip should be free from cracks, crevices, and similar defects which trap foreign matter and contamination and which are susceptible to propagation by stress corrosion; and
8. Proper jaw alignment should be maintained at all times to prevent shearing of the vascular tissue between the jaws.

These criteria are extremely important to the performance of the clip. Consequently, the clip design must ensure that the above criteria are met. In addition to the clip design, the process of manufacturing the clip also must ensure that the above criteria are met.

Some prior art designs require that holes be drilled, components be welded or riveted, or recesses be formed. Machining processes are often required. Such manufacturing procedures introduce unacceptable microcracks, voids, and crevices into the clip. Defects such as these are especially detrimental when titanium or titanium alloys are used to fabricate the clip because titanium is notch sensitive, susceptible to phase separation when machined, and prone to embrittlement and microcracking.

Specifically, sharp corners of recesses and the machining process used to form prior art clips can create and propagate microcracks in the metal surface, producing a clip undesirable for use as a cerebral implant. Drilled holes and riveted components render the clip susceptible to microcracks emanating radially from the holes and in the region of riveting. The consequent potential for propagating cracks and trapping unwanted contaminants in the cracks renders the clip unsafe for implantation. Welding poses problems of surface irregularities and the elevated temperatures required to weld alter the strength of a clip formed from titanium metal or titanium alloy. Moreover, welding of titanium is a difficult and expensive manufacturing operation requiring an inert atmosphere blanket. Thus, drilling, welding, riveting, and machining steps should be avoided in the processes of manufacturing a titanium aneurysm clip; otherwise, the clip produced cannot satisfy the criteria required for a desirable clip.

The surgical clip disclosed in U.S. Pat. No. 5,053,045 attempts to satisfy the above criteria. The clip includes a continuous, resilient member having a coil spring and two arms supporting clamping jaws. The coil spring forces the clamping jaws together. The member is titanium or a titanium alloy such as Ti 6-4. One arm has a guide section, through which the guided element of the second arm extends, to guide and restrict movement of the second arm for correctly engaging the clamping jaws. The '045 patent does not disclose a method of manufacturing the clip to ensure that the resulting design meets the above criteria. Nor does the patent disclose how the titanium or Ti 6-4 material is processed to avoid developing unacceptable microcracks, voids, and crevices during manufacture.

To overcome the shortcomings of known aneurysm clips, a new process of manufacturing such clips is provided. An object of the present invention is to provide a process of manufacturing an improved cerebral aneurysm clip which fully satisfies the criteria listed above. A related object is to avoid the problems noted above which are encountered with prior art manufacturing processes for aneurysm clips. Another object is to provide a manufacturing process which yields an improved cerebral aneurysm clip made entirely from titanium or a titanium alloy.

A more specific object of the present invention is to provide a manufacturing process which does not require drilling, welding, riveting, or machining steps. Therefore, unacceptable microcracks, voids, and crevices are not introduced into the clip. Because welding is not required, the inherent danger of altering the temper of the clip is avoided.

SUMMARY OF THE INVENTION

To achieve these and other objects, and in view of its purposes, the present invention provides a process of manufacturing an aneurysm clip having a coil spring, a first arm ending in a first clamping jaw, a first element connecting the first arm to the coil spring, a second arm ending in a second clamping jaw, and a second element connecting the second arm to the coil spring. The steps of the method include: (a) providing a solid, cylindrical starting rod of either titanium or titanium alloy; (b) cold drawing the starting rod to reduce its outside diameter and increase its strength; (c) cutting the starting rod to form a single, continuous, elongated, resilient member; (d) winding the member about a mandrel to form the coil spring, the winding providing the arms with a non-zero free angle predetermined to incorporate the deflection of the arms into the clamping force of the clip; (e) shaping the member into two end sections forming the clamping jaws and two connecting sections forming the connecting elements; (f) coining the two end sections of the member at a temperature between approximately 900° and 1000° F. to form the clamping jaws; and (g) bending the clamping jaws into a position assuring that said clamping jaws are substantially parallel when clamped onto tissue. The sequence of these processing steps may be changed to facilitate precision manufacturing.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing, in which.

DETAILED DESCRIPTION OF THE INVENTION

A. An Exemplary Surgical Clip

Figure 1:
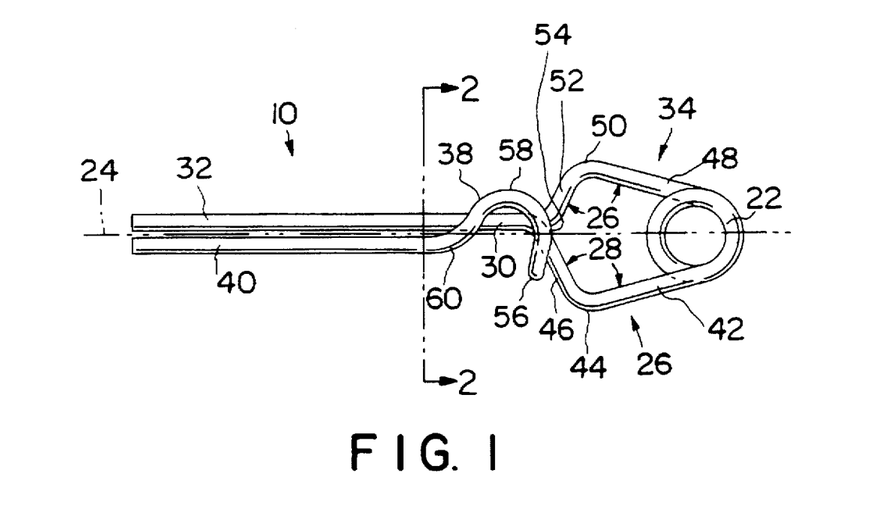
FIG. 1 illustrates a bottom view of an exemplary embodiment of a surgical clip manufactured in accordance with the process of the present invention.
Figure 2:
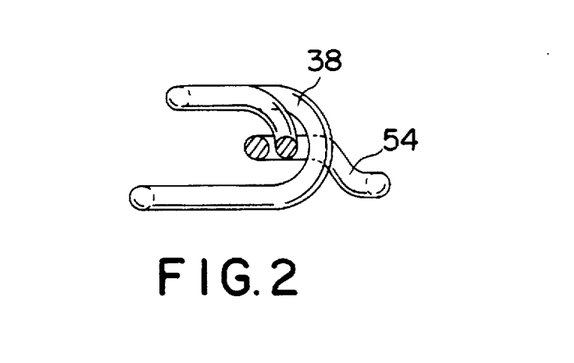
FIG. 2 is a cross-sectional view taken along the line 2—2 in FIG. 1.

Referring now to the drawing, wherein like reference numerals refer to like elements throughout, FIGS. 1 and 2 illustrate an exemplary surgical clip 10. Clip 10 was previously disclosed in U.S. Pat. No. 5,053,045 (see FIGS. 6 and 7) by the same inventors and can be formed using the process of the present invention. It is emphasized that the figures have not been drafted to scale and that dimensions have been arbitrarily expanded or reduced for clarity.

A coil spring 22 lies on longitudinal clip axis 24 at one end of clip 10. A first arm 26 extends away from spring 22 and comprises a first flex section 28, a guided element 30, and a first clamping jaw 32. A second arm 34 also extends away from spring 22, in a direction away from first arm 26, and comprises a second flex section 36, a guide section 38, and a second clamping jaw 40. Spring 22 is located between first flex section 28 and second flex section 36 so that it may urge first clamping jaw 32 and second clamping jaw 40 against each other.

First flex section 28 extends from spring 22 and is disposed lengthwise along axis 24. Flex section 28 includes a first straight length 42 integrally connected at one end to spring 22. First length 42 extends away from spring 22 at an oblique angle to axis 24 and is integrally connected to a first forceps-gripping elbow 44 at its opposite end. Flex section 28 also includes a second straight length 46 integrally connected at one end to first elbow 44 and integrally connected to guided element 30 at its opposite end, extending toward guided element 30 at an oblique angle to axis 24.

First flex section 28 thus forms a first forceps-gripping elbow 44 at the point in first arm 26 farthest from axis 24. When a force is placed on first elbow 44 directed toward axis 24, elbow 44 moves toward axis 24, causing first clamping jaw 32, which is located on the opposite side of axis 24 from flex section 28, to move away from second clamping jaw 40. When that force is removed, first elbow 44 returns to its initial position farthest from axis 24 and, consequently, first clamping jaw 32 returns to meet second clamping jaw 40. In this way, flex section 28 is resiliently deformable from its position with respect to axis 24.

Second flex section 36, substantially identical to flex section 28, extends from spring 22 and is disposed lengthwise along axis 24 substantially symmetrically with respect to flex section 28 about axis 24. Flex section 36 includes a third straight length 48 integrally connected at one end to spring 22. Third length 48 extends away from spring 22 at an oblique angle to axis 24 and is integrally connected to a second forceps-gripping elbow 50 at its opposite end. Flex section 36 also includes a fourth straight length 52 integrally connected at one end to second elbow 50 and integrally connected to guide section 38 at its opposite end, extending toward guide section 38 at an oblique angle to axis 24.

Second flex section 36 thus forms a second forceps-gripping elbow 50 at the point in second arm 34 farthest from axis 24. When a force is placed on second elbow 50 directed toward axis 24, elbow 50 moves toward axis 24, causing second clamping jaw 40, which is located on the opposite side of axis 24 from flex section 36, to move away from first clamping jaw 32. When that force is removed, second elbow 50 returns to its initial position farthest from axis 24 and, consequently, second clamping jaw 40 returns to meet first clamping jaw 32. In this way, flex section 36 is resiliently deformable from its position with respect to axis 24.

Guided element 30 of first arm 26 is integrally connected to first flex section 28 on one end and to first clamping jaw 32 on its opposite end. Element 30 makes a simple turn 54 between first elbow 44 of flex section 28 and jaw 32, extending through guide section 38 of second arm 34 and across axis 24.

Bent guide section 38 of second arm 34 is integrally connected to second flex section 36 on one end and to second clamping jaw 40 on its opposite end. Guide section 38 extends from flex section 36 and crosses axis 24 at an oblique angle to axis 24. Section 38 passes over guided element 30 and, at the point where guide section 38 is directly over guided element 30, section 38 and element 30 nearly, but do not, contact. Thus, element 30 is confined by section 38 and cannot move upward.

Guide section 38 then makes a reverse twist 56 which goes around guided element 30 so that section 38 is now underneath element 30 and directed back toward axis 24 at virtually the same oblique angle at which section 38 originally crossed axis 24 when above element 30. Reverse twist 56 is located so that jaws 32 and 40, when urged toward each other, will contact before guided element 30 would contact the inside surface of twist 56.

Guide surface 38 then forms a gradual, C-shaped loop 58 underneath guided element 30. Loop 58 crosses axis 24 twice. At the two points where loop 58 of guide section 38 is directly under guided element 30, section 38 and element 30 nearly, but do not, contact. The two points lie in an essentially common plane underneath element 30 on the opposite side of element 30 from the near-contact, movement-confining point on top of element 30. Thus, element 30 is confined by section 38 and cannot move downward. Guide section 38 then makes a final bend 60 so that section 38 is directed parallel to axis 24 and integrally connects with jaw 40. The manner in which guide section 38 confines guided element 30 is illustrated more specifically in FIG. 2.

In operation, when a force is placed on first forceps elbow 44 and second forceps elbow 50 directed toward axis 24, elbows 44 and 50 move toward axis 24. This action causes first clamping jaw 32 and second clamping jaw 40 to move away from each other. When the force is removed, first elbow 44 and second elbow 50 return to their initial position farthest from axis 24 and, consequently, second clamping jaw 40 returns to meet first clamping jaw 32.

B. The Starting Member Used to Produce the Clip

Figure 3:
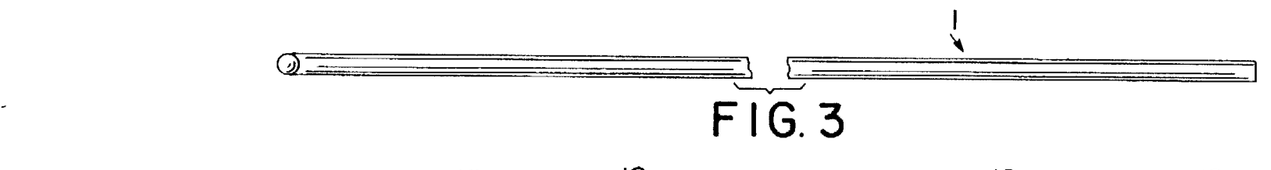
FIG. 3 shows the starting rod, from which the exemplary surgical clip is to be constructed in accordance with the process of the present invention, before the first processing step.
Figures 4, 5:
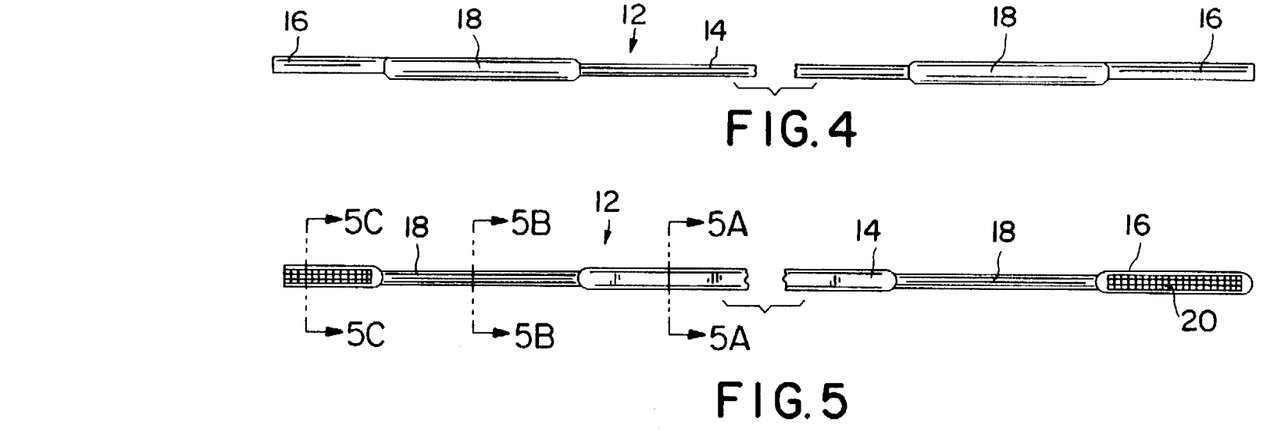
FIGS. 4 and 5 are top and side views, respectively, of the member following the cold drawing, cutting, and coining steps of the process of the present invention.

FIG. 3 shows a starting rod 1 from which surgical clip 10 is to be constructed in accordance with the process of the present invention. Starting rod 1 is a solid, cylindrical, round wire rod.

Preferably, starting rod 1 is made of titanium or a titanium alloy. Titanium has excellent resistance to corrosion, even in saline environments, at temperatures below about 800° F. The strength of alloys of titanium is from two to three times greater than that of aluminum alloys and equal to some of the steel alloys. In addition, titanium has greater stiffness than the aluminum alloys. Titanium and its alloys are nonmagnetic (thus preventing interference with magnetic resonance imaging of the body), inert, and biocompatible with body tissue and fluid. These properties make the use of titanium alloys very attractive.

Titanium exists in two allotropic forms, alpha at temperatures up to 1800° F. and beta above that temperature. Alpha titanium has an hexagonal structure; beta is body-centered cubic. Thus, there are three general types of titanium alloys depending upon the structures: all alpha, alpha and beta, and all beta.

The all-alpha alloys are not responsive to heat treatment and, thus, do not develop the strength possible in the other alloys through heat treatment. The beta alloys have relatively low ductility for strengths comparable to the other alloys. The alpha-beta alloys are heat-treatable, age-hardenable, strong, and possess good ductility. Although more formable than the alpha alloys, the alpha-beta alloys are not weldable without degradation. They lose ductility as a result of grain coarsening when heated above the alpha-beta transformation temperature. One particular alpha-beta titanium alloy, Ti 6-4, is the preferred alloy material for starting rod 1 if CP Titanium material is not used. An alloy of 6% aluminum, 7% niobium, and the remainder titanium is also suitable.

Because Ti 6-4 has two phases (alpha and beta), it is notch sensitive and has a tendency for surface imperfections to propagate as cracks. Cracks are likely to develop during deformation, such as occurs during coining, coiling, and bending operations. It has been shown that even fully annealed alpha-beta alloy starting rods tend to develop undesirable longitudinal cracks. The manufacturing process of the present invention prevents crack formation not only in Ti 6-4 alloy but in cold work hardened CP Titanium also.

C. Cold Drawing

Figure 6:
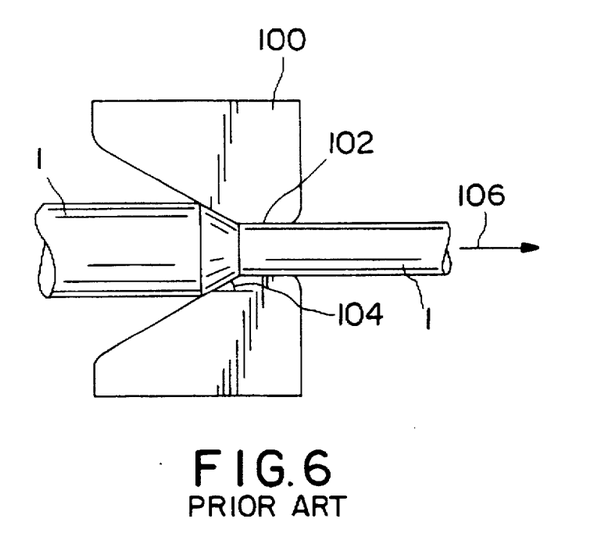
FIG. 6 is a cross section of a conventional drawing die used in the process of the present invention.

Starting rod 1 is cold drawn through a die 100, reducing the outside diameter of starting rod 1, as shown in FIG. 6. Die materials are usually alloy steels, carbides, and diamond. Among the important parameters involved in cold drawing starting rod 1 are the properties of the material used to form starting rod 1, the percent reduction in cross-sectional area desired (as defined by the opening in land 102), the die angle 104 and geometry, the amount of drawing force 106 (and, hence, the speed of drawing), and lubrication. The purpose of die land 102 is to maintain dimension-al accuracy. The operation consists of swaging the end of starting rod 1 to reduce the cross-sectional area so that starting rod 1 can be fed into die 100. Starting rod 1 is then pulled through die 100 at high speed. Typically, several dies 100 are used in tandem to reduce the diameter of starting rod 1 to the desired dimension.

Starting rod 1 is cold drawn to, for example, a 0.036-inch diameter. Cold drawing CP Titanium or Ti 6-4 as a step in the manufacturing process of clip 10 has produced unexpected increases in the clamping force of clip 10. Generally, spring calculations indicate that CP Titanium or Ti 6-4 aneurysm clips have a low maximum clamping force. For example, according to commonly used spring calculations, a 20 millimeter-long clip made of 0.92 millimeter (0.036 inch) wire rod will have a clamping force which is not expected to exceed 150 grams.

This limitation on the clamping force occurs because of the low elastic modulus of elasticity of the titanium (about $14.5 \times 10^6$ lb/in$^2$) or the Ti 6-4 (about $16.6 \times 10^6$ lb/in$^2$) material. These values are about one-half of the modulus of elasticity of Elgiloy or steel materials which are generally used to make aneurysm clips. Elgiloy and steel have a modulus of elasticity in the range of $28 \times 10^6$ to $30 \times 10^6$ lb/in$^2$.

It has been found, however, that clips made from CP Titanium or Ti 6-4 which are repeatedly cold drawn (reductions in diameter of over 50% have been achieved)

can have a highly desirable 180–250 gram clamping force range without plastic flow. The large increase in clamping force which results from repeated cold drawing is an unexpected and unforeseen result. It is believed that repeated cold drawing increases the "apparent" elastic modulus of the CP Titanium or Ti 6-4 material. Consequently, the ultimate tensile strength has been found to increase to about 145–155, 000 lb/in$^2$ after cold drawing for both CP Titanium and Ti 6-4. Conventional processes applied to increase yield stress and clamping force, such as heat or chemical treatment of Ti 6-4, have been found to be ineffectual. Specifically, cracks develop in the cold-worked spring material, while it is being coiled (as described below), despite such treatments.

Starting rod 1 is provided in long lengths, then cold worked as described above. Subsequently, starting rod 1 is cut into lengths suitable to form a properly sized member 12 from which clip 10 will ultimately be formed. The length of member 12 is typically about 2.5 to 3 inches. Thus, clip 10 is formed from a single, continuous, elongated, resilient member 12.

D. Coining

After it is formed by cold drawing and cut to size, member 12 is bent, shaped, and coined (as described below) to form clip 10. Although the two end sections (which form the clamping jaws) must be coined for all clips, coining of the center section (which forms the coil spring) is optional and is done only when a maximum closing force is desired (over 200 grams). The process including the step of coining the center section is described first.

Member 12 is coined to form the three differently shaped sections shown in FIGS. 2 and 3: a center section 14 (of about 0.65 inches in length, for example) which is used to form coil spring 22, two end sections 16 which are used to form clamping jaws 32 and 40, and two connecting wire sections 18 which are used to form the remaining elements of clip 10. The point which forms one end of clip 10 is chosen, using the example dimensions, at a position about 1.05 inches from one end of member 12. An off-center position is chosen because first arm 26 requires fewer turns than second arm 34 and the two arms should end at the same point.

Coining is a cold metalworking process done in a press-type die. The process is used to form raised sections, serrations, and other details. The die applies high pressure to the metal workpiece, thereby forcing the metal to flow plastically into the die details. The absence of overflow of excess metal from between the die halves is characteristic of coining and is responsible for the fine detail achieved.

Figure 5A:
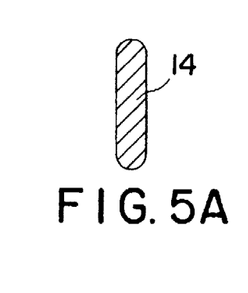
FIGS. 5a, 5b, and 5c are cross-sectional views taken, respectively, along lines 5a, 5b, and 5c of FIG. 5.
Figure 5B:
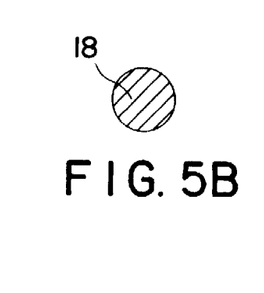
Figure 5C:
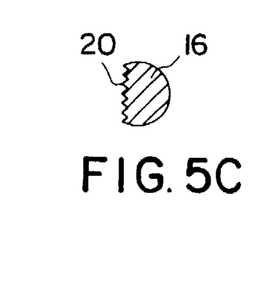

As shown in FIG. 5a, center section 14 is flattened, creating an oval from which coil spring 22 is formed. Suitable dimensions for the oval are 0.030 inches by 1.050 inches. Connecting sections 18 retain the round-wire shape, as shown in FIG. 5b and, thus, in the example used, remain circular with a diameter of 0.036 inches. End sections 16 are coined to form, as shown in FIG. 5c, flat faces 20 with serrations to grasp tissue between the two faces. Faces 20 may be 0.040-inches wide and the maximum depth from face 20 to the apex of the curved portion of section 16 is then 0.032 inches.

All of the dimensions provided are examples only, based on the starting size of member 12 chosen to form a typically sized surgical clip 10. Different dimensions are necessary, of course, to form differently sized clips. The size of member 12 must be sufficiently small, of course, to form a clip suitable for cerebral implantation.

Figure 7:
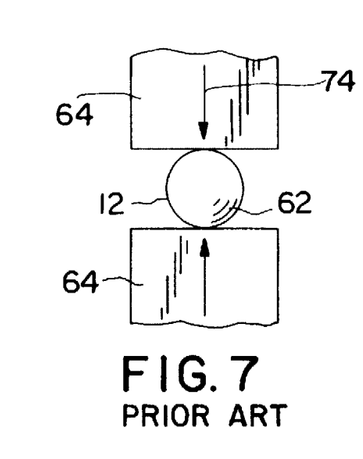
FIG. 7 illustrates a conventional coining die having flat surfaces.
Figures 8, 9, 10:
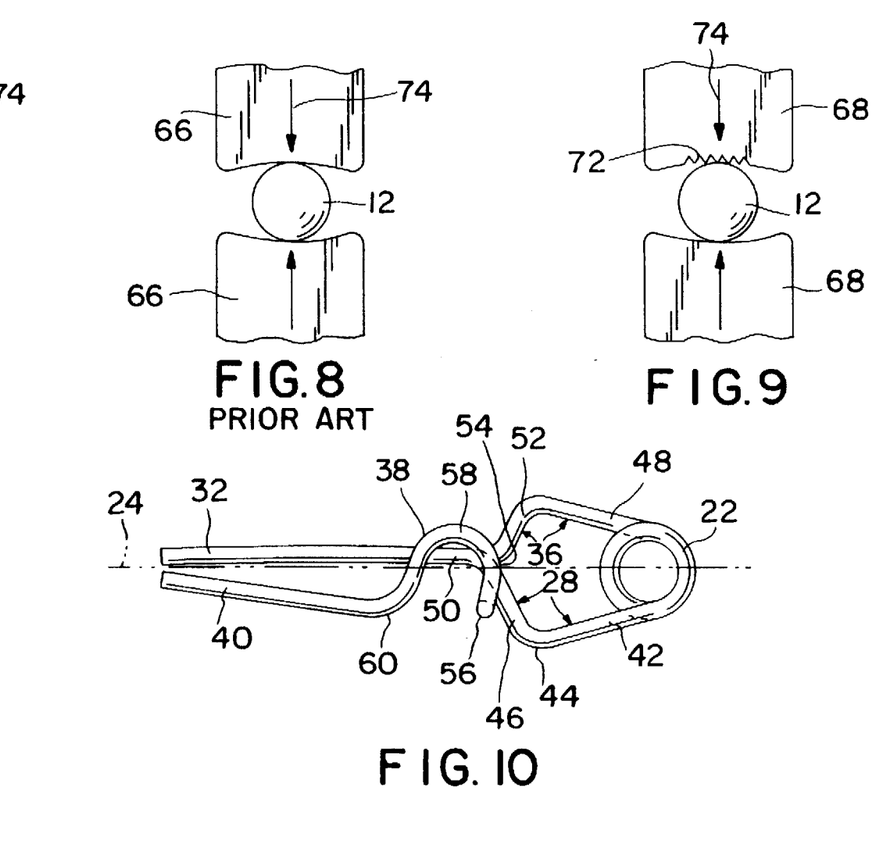
FIG. 8 illustrates an improved coining die having concave surfaces.
FIG. 9 illustrates an improved coining die having concave surfaces and a serrated face.
FIG. 10 depicts the phenomenon of "fish tailing" in which the clamping jaws of the clip bend toward each other because they are insufficiently rigid to resist such bending.

The coining step of the process is done with coining dies as illustrated in FIGS. 7, 8, and 9. Such dies provide member 12 at different sections along its length with the desired cross-sectional configurations and dimensions discussed above. The step may be completed with a single, elongated coining die having segments which are differently configured at different sections along its length to provide sections 14, 16, and 18 on member 12. Using such a die, a single coining operation can accomplish the required shaping and sizing of the blank starting member 12 along its length. Preferably, for reasons discussed below, multiple, separate coining operations may be completed on the starting member 12 at the different sections 14, 16, and 18.

On highly cold worked CP Titanium or Ti 6-4, cracks are likely to develop during additional deformation, such as occurs during the coining operation and upon coiling spring 22 and bending first arm 26 and second arm 34. To provide ductility and to help prevent cracks on coining, bending, and shaping, the titanium literature suggests that member 12 should be annealed by heating it to 1250°–1300° F., holding for 5–10 minutes, then air cooling. It was found, however, that even fully annealed alpha-beta alloy starting members 12 developed unacceptable longitudinal cracks 62 when conventional coining dies 64 having flat surfaces as shown in FIG. 7 are used. Stress analysis revealed that cracks 62 are caused by elastic buckling, which causes failure in lateral shear.

U.S. Pat. No. 4,765,335 disclosed the discovery, by the same inventors, that a concave coining die 66 (see FIG. 8) provided an effective buckling restraint and prevented shears. Accordingly, cracks were avoided. Concave die 66 distributes the load and prevents lateral shear while flowing the metal. Approximately 50% reductions in the diameter of titanium alloy starting member 12 were obtained (from 0.035 inches down to 0.020–0.025 inches) in a room temperature coining operation without developing cracks. The slope of the concave die surface depends on the desired percentage of deformation and can be calculated by a person skilled in the art of stress analysis.

It was also found that, by heating member 12 to an elevated temperature during the coining operation, greater deformation of the titanium alloy member 12 could be achieved while avoiding the development of cracks 62. The '335 patent taught that titanium and titanium alloy parts heated to 600°–700° F.—but not in excess of 800° F.—permitted approximately a 40% reduction in the starting rod diameter, even without using concave die 66, while minimizing the number of cracks 62.

Temperatures in excess of 800° F. were thought to be ill-advised for coining, however, because it was believed that the beta phase transitus temperature of the alpha beta titanium alloy set a practical upper limit to heating. Furthermore, accepted design practices for torsion springs advise against stress relieving (which occurs above 800° F.) because the residual coiling stresses tend to increase the elastic limit for these springs. Titanium and its alloys also have the disadvantage of reacting with other elements at temperatures above 800° F. The reaction characteristics of titanium at elevated temperatures cause considerable difficulties in forming operations as well as in its initial production.

The '335 patent also noted that only center section 14 of member 12 which forms coil spring 22 requires the special coining operation (concave die 66 plus heating) described. Sections 16 and 18 could be shaped and dimensioned with conventional coining operations using flat coining dies 64, the '335 patent taught, because those sections did not require as much deformation as center portion 14.

It has since been found, however, that cracks 62 still developed in end sections 16 of member 12 when end sections 16 were coined as taught by the '335 patent. End sections 16 are coined to form flat faces 20 with serrations to assure that clip 10 grips tissue without slipping. Cracks 62 were found to develop in end sections 16 as long as the coining temperature was below 900° F. It was discovered, however, that cracks 62 disappeared above 900° F. Although the frequency of crack formation starts to decrease at coining temperatures above 700° F., some cracking remains even at 875° F.

An upper processing temperature limit of 1000° F. 10 exists for heating member 12 during the coining operation. Coining temperatures in excess of 1000° F. require a protective atmosphere. When member 12 is coined above 1000° F., member 12 loses stiffness (rigidity) due to partial annealing and clamping jaws 32, 40 tend to "fish tail"—an undesirable effect. (Illustrated in FIG. 10. "fish tailing" describes a phenomenon in which clamping jaws 32, 40 bend toward each other at their ends because they are insufficiently rigid to resist such bending.) Furthermore, stress relief is complete at such temperatures and, as noted above, stress relieving should be avoided for torsion springs. Coining in the 900°–1000° F. region is contrary, therefore, to conventional metallurgical practices for torsion springs. The resulting benefit of increased strength is unexpected.

Multiple, separate coining operations are preferable on starting member 12 at the different sections 14 and 16 because each section requires different processing to assure optimum qualities for the clip 10 produced. To coin end sections 16, for example, a concave die 68 having a serrated face 72 (shown in FIG. 9) is used. Die 68 is heated to a temperature between 900° F. and 1000° F. One end of member 12 is inserted into die 68 and the metal is allowed to reach the temperature of die 68. A force 74 of between about 5–10,000 lb. is applied to press die 68 into member 12 and form the cross-section shown in FIG. 5c. Subsequently, member 12 is removed from die 68, rotated 180 degrees, and an identical operation is performed on the opposite end of member 12.

The serrations of face 20 illustrated in FIG. 5c provide non-slip gripping of vessel 70. The serrations also increase the stiffness of clamping jaws 32, 40. Such increased stiffness is not required when clip 10 is made of Elgiloy or steel.

As noted above, coining of center section 14 (which forms coil spring 22) is optional. If center section 14 is not coined, then member 12 is shaped as discussed below before any coining operation. End sections 16 are coined after member 12 is shaped, but before clamping jaws 32, 40 are bent into their final position to form clip 10. Alternatively, if center section 14 is coined before coil spring 22 is wound, then member 12 is shaped as discussed below after that coining operation. End sections 16 may still be coined after member 12 is shaped, but before clamping jaws 32, 40 are bent into their final position to form clip 10.

E. Shaping and Bending

Figure 11A:
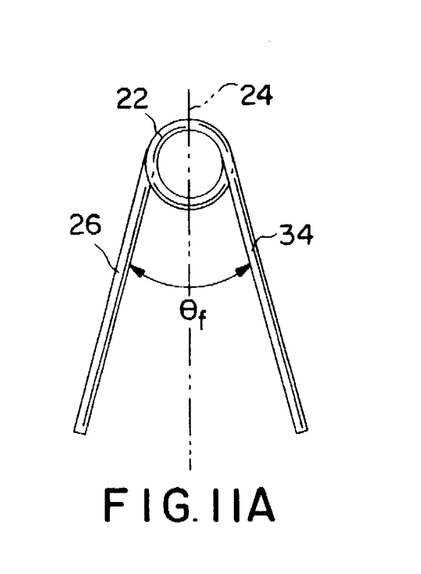
FIGS. 11a through 11f illustrate the starting member as the various steps of bending and shaping are applied to form the clip shown in FIG. 1.

As shown in FIGS. 11a–11f, member 12 is shaped and bent to form the clip 10 of FIG. 1. The first step is the spring winding process to form centrally located coil spring 22. Coil spring 22 is formed by winding member 12 about a mandrel. Coil spring 22 gives clip 10 resiliency and causes clamping jaws 32, 40 to close on themselves as described above. Coil spring 22 can be wound cold or can be heated to a temperature between 800°–1000° F. and then wound. When cold formed, CP Titanium or Ti 6-4 coil spring hardens as evidenced by an approximately 5–10,000 lb/in$^2$ increase in ultimate tensile strength. Member 12 will appear as depicted in FIG. 11a following formation of coil spring 22.

As shown in FIG. 11a, coil spring 22 is formed on longitudinal clip axis 24. First arm 26 extends away from coil spring 22. Second arm 34 also extends away from coil spring 22 and in a direction away from first arm 26. First arm 26, second arm 34, and coil spring 22 lie in substantially the same plane.

Figure 11B:
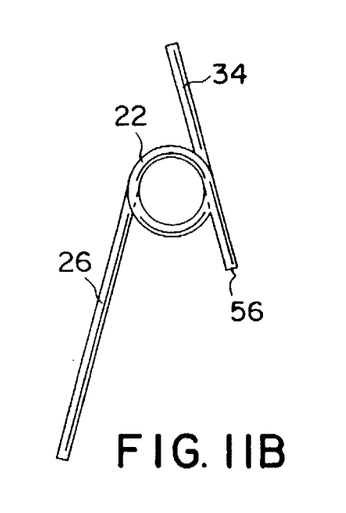
Figure 11C:
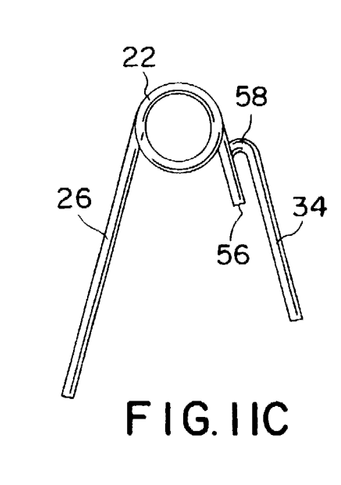
Figure 11D:
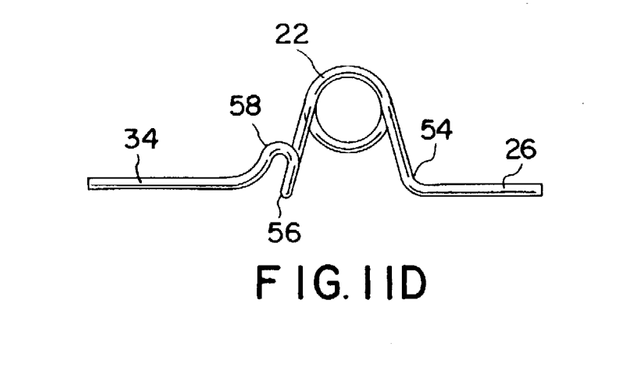
Figure 11E:
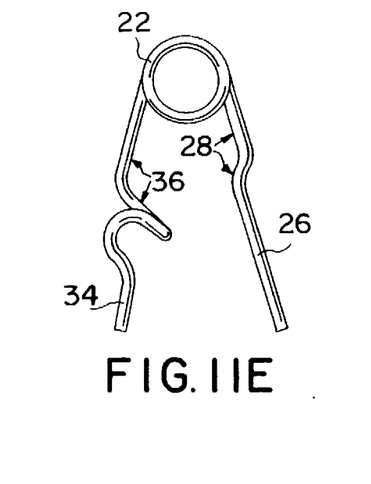
Figure 11F:
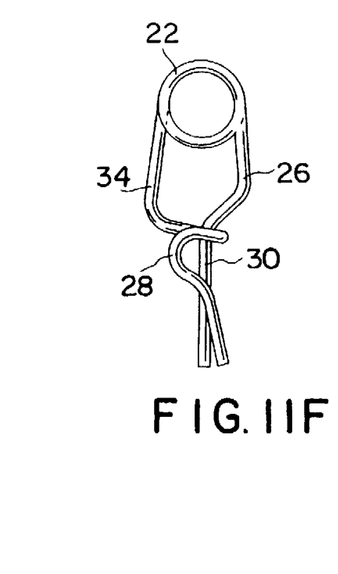

As shown in FIG. 11b, reverse twist 56 is then shaped in second arm 34. FIG. 11c shows that gradual, C-shaped loop 58 is next shaped in second arm 34. Next, member 12 is shaped to form turn 54 in first arm 26 (FIG. 11d). First arm 26 and second arm 34 are shaped to form, respectively, first flex section 28 and second flex section 36 (FIG. 11e). Finally, first arm 26 and second arm 34 are bent towards each other so that guided element 30 can be disposed in guide section 38 as shown in FIG. 11f.

Typically, end sections 16 are coined after member 12 is shaped as shown in step 11e, but before clamping jaws 32, 40 are bent into their final position (step 11f) to form clip 10.

Preferably, the stresses induced in member 12 following each of the coining, coiling, shaping, and bending operations discussed above need not be relieved by heat treatment.

For the Ti 6-4 alloy, member 12 can be strengthened by solution treatment and aging. Solution treatment is done by heating member 12 to a temperature between 1500°–1750° F. (just below the beta transformation temperature) which produces the beta phase, holding for one hour, then water quenching to retain the beta phase. Member 12 is aged at 900°–1000° F. for 1–12 hours to decompose the unstable, supersaturated beta phase, then slow cooled in air to precipitate alpha particles. Care must be taken to prevent averaging, which lowers strength. If necessary, member 12 can be softened by heating it to 1300° F. for 1 hour.

F. Arm Deflection and Parallel Clamping Jaws

Conventional processes used to manufacture aneurysm clips achieve a desired clamping force by winding spring coil 22 to a predetermined free angle $\theta_f$ (see FIG. 11a). Free angle $\theta_f$ is the angle between first arm 26 and second arm 34 of coil spring 22 when no load "P" is applied to coil spring 22. Absent load P, coil spring 22 does not deflect, stores no energy, and is inoperative. Typically, (1) the free angle of conventional clips is not designed to incorporate the deflection of the arms into the clamping force of the clip, and (2) the clamping jaws of conventional clips diverge slightly (are not substantially parallel) when the clip is clamped onto a blood vessel. Neither of these aspects of conventional clip designs are advisable for clips manufactured from CP Titanium or Ti 6-4 alloy, in part, because they lack sufficient rigidity to prevent the fish-tailing phenomenon illustrated in FIG. 10. The fish-tailing phenomenon is not a problem for Elgiloy and steels because these materials are inherently more rigid than is Ti 6-4.

1. Incorporating Arm Deflection Into Free Angle of Clip

Helical torsion springs such as coil spring 22 store energy when a load is applied and the spring is deflected. First arm 26 and second arm 34 of coil spring 22 provide a means of loading or deflecting the spring. The relation of the load (pounds) to the deflection (inches) of the torsion spring, the spring gradient, K, is expressed in terms of pound-inches per degree of motion.

Ordinarily, in designing and manufacturing aneurysm clips, it is customary to disregard the deflection of the arms in designing the clamping force of the clip. Thus, conventional designs consider only the contribution of the coil to the clamping force and the clip is manufactured to that design. This may be appropriate for clips manufactured from relatively rigid materials such as Elgiloy and steel. For relatively flexible clips made of Ti 6-4, however, such a design and manufacture procedure introduces an appreciable error and, therefore, is inappropriate.

Figure 12:
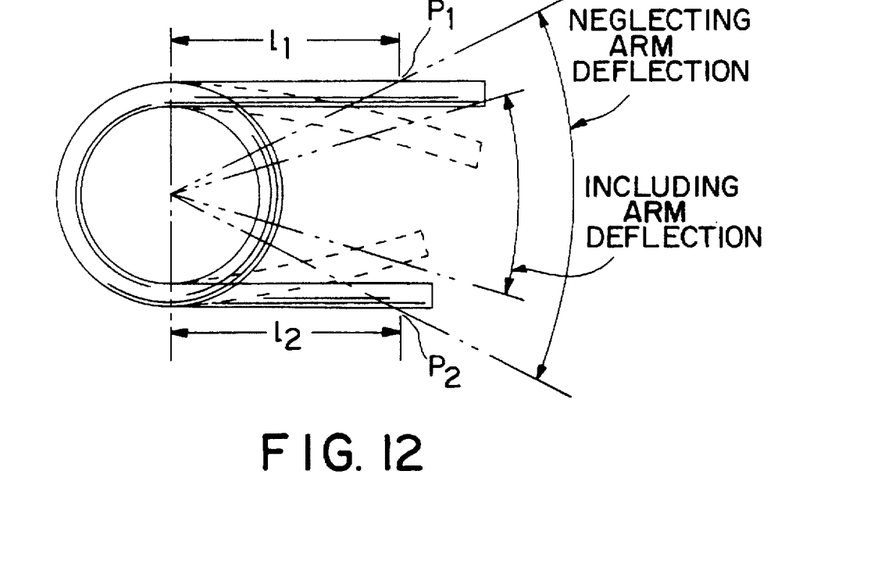
FIG. 12 illustrates the error, overcome by the process of the present invention, introduced when the deflection of the clamping jaws is disregarded in designing the clamping force of the clip.

The error is illustrated in FIG. 12. Note that the spring arms, deflecting as cantilever beams, increase the total deflection under a given loading ($P_1$ and $P_2$). Especially when larger loads are applied, the clamping force of the clip is derived largely from the resistance of the arms to bending and is relatively independent of the force developed by the coil spring itself. In the manufacturing process of the present invention, the effect of arm deflection is incorporated into the clip clamping force through predetermined design of free angle $\theta_f$.

Without including arm deflection, the formula for gradient K is:

$$K=(E \times d^4) \div (1170 \times L),$$

where E is the modulus of elasticity, about $16.6 \times 10^6$ lb/in$^2$ for Ti 6-4; d is the diameter of coil spring 22 (about 0.035 inches, for example); and L is the total length of coil spring 22, including the coil and arms (about 2.5 inches, for example). When arm deflection is included, the formula is modified:

$$K=(E \times d^4) \div (1170 \times (L_b + l_1/3 + l_2/3)),$$

where $L_b$ is the "active" length of the body of the spring and $l_1$ and $l_2$ are lengths (inches) as shown in FIG. 12. (In springs with many coils and short arms, unlike the case of aneurysm clips, the effect of $l_1/3 + l_2/3$ is negligible.) The above formulas are recited in Spring Design Data, Section 4, page 4 (1964), published by Ametek, Inc. of Hatfield, Pa.

By taking into account the deflection of first arm 26 and second arm 34, the spring gradient K decreases. The moment or torque, M (pound-inches), is related to the angular deflection, $\phi$ (degrees), by $M=K \times \phi$. Therefore, a lesser spring gradient K allows a larger angle $\phi$ for the same moment or torque M.

2. Parallel Clamping Jaws

In conventional designs, the relatively rigid clamping jaws of the clip, substantially parallel when closed, are not substantially parallel when the clip is clamped onto a blood vessel. Specifically, the ends of the clamping jaws will diverge slightly—pushed apart about 0.25 mm (0.010 inches)—after contacting the vessel. Consequently, the clamping force which the clamping jaws exert on that vessel is non-uniform and the conventional clip risks slipping off the vessel.

Figure 13:
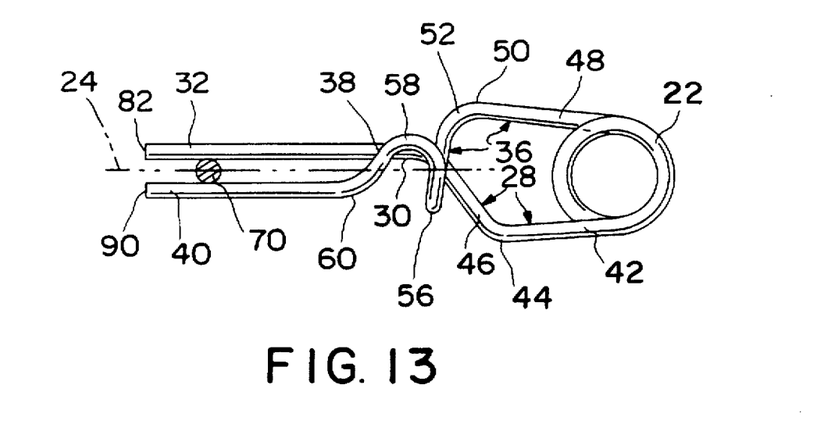
FIG. 13 illustrates the parallel position of the clamping jaws, of a clip manufactured in accordance with the present invention, when contacting a blood vessel.

As manufactured in accordance with the present invention, the relatively flexible clamping jaws 32, 40 of clip 10 assume a non-parallel position having slightly converging ends when clip 10 is opened slightly. The ends of clamping jaws 32, 40 are about 0.25 mm (0.010 inches) closer together than they would be if clamping jaws 32, 40 were perfectly parallel. When closed in contact with the vessel 70 (which typically has a diameter of 1–2 mm), as shown in FIG. 13, first end 82 of first clamping jaw 32 and second end 90 of second clamping jaw 40 will be substantially parallel. Clamping jaws 32, 40, non-parallel when opened slightly, assume a substantially parallel position upon closing onto vessel 70. Consequently, the clamping force which clamping jaws 32, 40 exert on vessel 70 is uniform and the risk of slippage is reduced. Most significantly, this feature provides a safe upper limit to the pressure applied to vessel 70 by clip 10 and reduces the danger of necrosis of the tissue due to excessive pressure.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention. Specifically, it is believed evident to one skilled in the art of manufacturing aneurysm clips that the physical dimensions of the clips constructed according to the present invention can be modified easily to produce clips in the full size and shape ranges used for cerebral aneurysm clips. The sequence of processing steps can be varied to accommodate precision manufacturing requirements.

We claim:

1. A process of manufacturing an aneurysm clip having, a coil spring, a first arm ending in a first clamping jaw, a first element connecting the first arm to the coil spring, a second arm ending in a second clamping jaw, and a second element connecting the second arm to the coil spring, said method comprising:

providing a solid, cylindrical starting rod of one of titanium and titanium alloy;

cold drawing said starting rod to reduce the outside diameter of said starting rod and increase the strength of said starting rod to an ultimate tensile strength of at least 145,000 lb/in$^2$;

cutting said starting rod to form a single, continuous, elongated, resilient member;

shaping said member into a center section forming the coil spring, two end sections forming the clamping jaws, and two connecting sections forming the connecting elements;

coining the two end sections of said member to form the clamping jaws; and bending said clamping jaws to form the clip.

2. The process according to claim 1 wherein said starting rod is Ti 6-4.

3. The process according to claim 1 wherein said aneurysm clip is manufactured without any one of drilling, welding, riveting, and machining said member.

4. The process according to claim 1 wherein the step of coining the two end sections of said member to form the clamping jaws is done at a temperature between approximately 900° and 1000° F.

5. The process according to claim 4 further comprising the additional step, after said step of cutting and before said step of shaping, of coining said member to form the center section used to form the coil spring, said additional step including:

providing a first curved coining die;

maintaining said first curved coining die at a temperature between approximately ambient and 1000° F.;

inserting said member into said first curved coining die;

allowing said member to reach the temperature of said first curved coining die; and activating said first curved coining die to form the center section used to form the coil spring.

6. The process according to claim 5 wherein said step of coining said member at a temperature between approximately 900° and 1000° F. to form the two end sections used to form the clamping jaws includes:

providing a second curved coining die having a serrated face;

maintaining said second curved coining die at a temperature between approximately 900° and 1000° F.;

inserting said member into said second curved coining die;

allowing said member to reach the temperature of said second curved coining die; and activating said second curved coining die to form the two end sections used to form the clamping jaws.

7. The process according to claim 6 wherein said step of activating said second curved coining die to form the two end sections used to form the clamping jaws includes pressing said die against said member with a force of about 5–10,000 pounds.

8. The process according to claim 4 wherein said step of coining said member at a temperature between approximately 900° and 1000° F. to form the two end sections used to form the clamping jaws includes:

providing a second curved coining die having a serrated face;

maintaining said second curved coining die at a temperature between approximately 900° and 1000° F.;

inserting said member into said second curved coining die;

allowing said member to reach the temperature of said second curved coining die; and activating said second curved coining die to form the two end sections used to form the clamping jaws.

9. The process according to claim 8 wherein said step of activating said second curved coining die to form the two end sections used to form the clamping jaws includes pressing said die against said member with a force of about 5–10,000 pounds.

10. The process according to claim 1 wherein said step of shaping said member includes winding said member about a mandrel to form the coil spring, said winding providing the arms with a non-zero free angle predetermined to incorporate the deflection of the arms into the clamping force of the clip.

11. The process according to claim 10 wherein said step of winding said member about a mandrel to form the coil spring is done while said member is maintained at a temperature between approximately 800° and 1000° F.

12. The process according to claim 1 wherein said clamping jaws are bent to a position assuring that said clamping jaws are substantially parallel when clamped onto tissue.

13. The process according to claim 1 further comprising the steps of (a) heating said member to a temperature between approximately 1500°–1750° F., holding said member at that temperature for approximately 1 hour, then water quenching said member to solution treat said member; and (b) heating said member to a temperature between approximately 900° and 1000° F., holding said member at that temperature for approximately 1 to 12 hours, then air cooling said member to age said member.

14. The process according to claim 1 further comprising the step of heating said member at a temperature between approximately 1250°–1300° F., holding for 5–10 minutes, then air cooling said member to anneal said member.

15. A process of manufacturing an aneurysm clip having a coil spring, a first arm ending in a first clamping jaw, a first element connecting the first arm to the coil spring, a second arm ending in a second clamping jaw, and a second element connecting the second arm to the coil spring, said method comprising:

providing a single, continuous, solid, elongated, resilient, cylindrical member of one of titanium and titanium alloy;

shaping said member into a center section forming the coil spring, two end sections forming the clamping jaws, and two connecting sections forming the connecting elements;

coining the two end sections of said member at a temperature between approximately 900° and up to 1000° F. to form the clamping jaws; and bending said clamping jaws to form the clip.

16. The process according to claim 15 further comprising the additional step, before said step of shaping, of coining said member to form the center section used to form the coil spring, said additional step including:

providing a first curved coining die;

maintaining said first curved coining die at a temperature between approximately ambient and 1000° F.;

inserting said member into said first curved coining die;

allowing said member to reach the temperature of said first curved coining die; and activating said first curved coining die to form the center section used to form the coil spring.

17. The process according to claim 16 wherein said step of coining said member at a temperature between approximately 900° and 1000° F. to form two end sections used to form the clamping jaws includes:

providing a second curved coining die having a serrated face;

maintaining said second curved coining die at a temperature between approximately 900° and 1000° F.;

inserting said member into said second curved coining die;

allowing said member to reach the temperature of said second curved coining die; and activating said second curved coining die to form the two end sections used to form the clamping jaws.

18. The process according to claim 17 wherein said step of activating said second curved coining die to form the two end sections used to form the clamping jaws includes pressing said die against said member with a force of about 5–10,000 pounds.

19. The process according to claim 15 wherein said step of coining said member at a temperature between approximately 900° and 1000° F. to form two end sections used to form the clamping jaws includes:

providing a second curved coining die having a serrated face;

maintaining said second curved coining die at a temperature between approximately 900° and 1000° F.;

inserting said member into said second curved coining die;

allowing said member to reach the temperature of said second curved coining die; and activating said second curved coining die to form the two end sections used to form the clamping jaws.

20. The process according to claim 19 wherein said step of activating said second curved coining die to form the two end sections used to form the clamping jaws includes pressing said die against said member with a force of about 5–10,000 pounds.

21. The process according to claim 15 wherein said member is Ti 6-4.

22. The process according to claim 15 wherein said aneurysm clip is manufactured without any one of drilling, welding, riveting, and machining said member.

23. The process according to claim 15 wherein said step of shaping said member includes winding said member about a mandrel while said member is maintained at a temperature between approximately 800° and 1000° F. to form the coil spring, said winding providing the arms with a non-zero free angle predetermined to incorporate the deflection of the arms into the clamping force of the clip, and wherein said clamping jaws are bent to a position assuring that said clamping jaws are substantially parallel when clamped onto tissue.

24. The process according to claim 15 further comprising the steps of (a) heating said member to a temperature between approximately 1500°–1750° F., holding said member at that temperature for approximately 1 hour, then water quenching said member to solution treat said member; and (b) heating said member to a temperature between approximately 900° and 1000° F., holding said member at that temperature for approximately 1 to 12 hours, then air cooling said member to age said member.

25. The process according to claim 15 further comprising the step of heating said member at a temperature between approximately 1250°–1300° F., holding for 5–10 minutes, then air cooling said member to anneal said member.

26. A process of manufacturing an aneurysm clip having a coil spring, a first arm ending in a first clamping jaw, a first element connecting the first arm to the coil spring, a second arm ending in a second clamping jaw, and a second element connecting the second arm to the coil spring, said arms exhibiting a deflection when a load is applied thereto, said method comprising:
    providing a single, continuous, solid, elongated, resilient, cylindrical member of one of titanium and titanium alloy;
    winding said member about a mandrel to form the coil spring, said winding providing the arms with a non-zero free angle therebetween which is predetermined to incorporate the deflection of the arms into the clamping force of the clip; and
    bending said clamping jaws to a position assuring that said clamping jaws are substantially parallel when clamped onto tissue.

27. The process according to claim 26 wherein said step of winding said member about a mandrel to form the coil spring is done while said member is maintained at a temperature between approximately 800° and 1000° F.

28. The process according to claim 26 further comprising the additional step, after said step of winding and before said step of bending, of shaping said member into two end sections forming the clamping jaws and two connecting sections forming the connecting elements.

29. The process according to claim 26 further comprising the steps of (a) heating said member to a temperature between approximately 1500°–1750° F., holding said member at that temperature for approximately 1 hour, then water quenching said member to solution treat said member; and (b) heating said member to a temperature between approximately 900° and 1000° F., holding said member at that temperature for approximately 1 to 12 hours, then air cooling said member to age said member.

30. The process according to claim 26 further comprising the step of heating said member at a temperature between approximately 1250°–1300° F., holding for 5–10 minutes, then air cooling said member to anneal said member.

31. The process according to claim 26 wherein said member is Ti 6-4.

32. The process according to claim 26 wherein said aneurysm clip is manufactured without any one of drilling, welding, riveting, and machining said member.

33. A process of manufacturing an aneurysm clip having a coil spring, a first arm ending in a first clamping jaw, a first element connecting the first arm to the coil spring, a second arm ending in a second clamping jaw, and a second element connecting the second arm to the coil spring, said arms exhibiting a deflection when a load is applied thereto, said method comprising:
    providing a solid, cylindrical starting rod of one of titanium and titanium alloy;
    cold drawing said starting rod to reduce the outside diameter of said starting rod and increase the strength of said starting rod to an ultimate tensile strength of at least 145,000 lb/in$^2$;
    cutting said starting rod to form a single, continuous, elongated, resilient member;
    winding said member about a mandrel to form the coil spring, said winding providing the arms with a non-zero free angle therebetween which is predetermined to incorporate the deflection of the arms into the clamping force of the clip;
    shaping said member into two end sections forming the clamping jaws and two connecting sections forming the connecting elements;
    coining the two end sections of said member at a temperature between approximately 900° and up to 1000° F. to form the clamping jaws; and
    bending said clamping jaws to a position assuring that said clamping jaws are substantially parallel when clamped onto tissue.

34. The process according to claim 33 wherein said member is Ti 6-4.

35. The process according to claim 33 wherein said aneurysm clip is manufactured without any one of drilling, welding, riveting, and machining said member.

36. The process according to claim 33 further comprising the additional step, after said step of cutting and before said step of winding, of coining said member to form the center section used to form the coil spring, said additional step including:
    providing a first curved coining die;
    maintaining said first curved coining die at a temperature between approximately ambient and 1000° F.;
    inserting said member into said first curved coining die;
    allowing said member to reach the temperature of said first curved coining die; and
    activating said first curved coining die to form the center section used to form the coil spring.

37. The process according to claim 36 wherein said step of coining said member at a temperature between approximately 900° and 1000° F. to form the two end sections used to form the clamping jaws includes:
    providing a second curved coining die having a serrated face;
    maintaining said second curved coining die at a temperature between approximately 900° and 1000° F.;
    inserting said member into said second curved coining die;
    allowing said member to reach the temperature of said second curved coining die; and
    activating said second curved coining die to form the two end sections used to form the clamping jaws.

38. The process according to claim 37 wherein said step of activating said second curved coining die to form the two end sections used to form the clamping jaws includes pressing said die against said member with a force of about 5–10,000 pounds.

39. The process according to claim 33 wherein said step of coining said member at a temperature between approximately 900° and 1000° F. to form the two end sections used to form the clamping jaws includes:

provided a second curved coining die having a serrated face;

maintaining said second curved coining die at a temperature between approximately 900° and 1000° F.;

inserting said member into said second curved coining die;

allowing said member to reach the temperature of said second curved coining die; and activating said second curved coining die to form the two end sections used to form the clamping jaws.

40. The process according to claim 39 wherein said step of activating said second curved coining die to form the two end sections used to form the clamping jaws includes pressing said die against said member with a force of about 5–10,000 pounds.

41. The process according to claim 33 wherein said step of winding said member about a mandrel to form the coil spring is done while said member is maintained at a temperature between approximately 800° and 1000° F.

42. The process according to claim 33 further comprising the steps of (a) heating said member to a temperature between approximately 1500°–1750° F., holding said member at that temperature for approximately 1 hour, then water quenching said member to solution treat said member; and (b) heating said member to a temperature between approximately 900° and 1000° F., holding said member at that temperature for approximately 1 to 12 hours, then air cooling said member to age said member.

43. The process according to claim 33 further comprising the step of heating said member at a temperature between approximately 1250°–1300° F., holding for 5–10 minutes, then air cooling said member to anneal said member.

44. The process according to claim 1 wherein said starting rod is an alloy of 6% aluminum, 7% niobium, and the remainder titanium.

45. The process according to claim 15 wherein said member is an alloy of 6% aluminum, 7% niobium, and the remainder titanium.

46. The process according to claim 26 wherein said member is an alloy of 6% aluminum, 7% niobium, and the remainder titanium.

47. The process according to claim 33 wherein said member is an alloy of 6% aluminum, 7% niobium, and the remainder titanium.

* * * * *